United States Patent
Wadström

(10) Patent No.: US 6,440,427 B1
(45) Date of Patent: Aug. 27, 2002

(54) TISSUE TREATMENT COMPOSITION COMPRISING FIBRIN OR FIBRINOGEN AND BIODEGRADABLE AND BIOCOMPATIBLE POLYMER

(75) Inventor: Jonas Wadström, Uppsala (SE)

(73) Assignee: Biovitrum AB, Stockholm (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/999,137

(22) Filed: Dec. 19, 1997

Related U.S. Application Data

(63) Continuation of application No. 08/780,442, filed on Jan. 8, 1997, now abandoned, which is a continuation of application No. 08/162,078, filed as application No. PCT/SE92/00441 on Jun. 17, 1992, now Pat. No. 5,631,011.

(30) Foreign Application Priority Data

Jun. 17, 1991 (SE) ............................................. 9101853

(51) Int. Cl.⁷ ............................ A61K 9/00; A61K 9/08; A61K 38/00

(52) U.S. Cl. ..................... 424/400; 424/422; 424/423; 424/424; 424/425; 424/426; 424/443; 514/21; 514/54

(58) Field of Search ................................ 424/400, 622, 424/423–426, 443, 484; 514/21

(56) References Cited

U.S. PATENT DOCUMENTS

| | | | | |
|---|---|---|---|---|
| 4,600,574 A | * | 7/1986 | Lindner | 424/28 |
| 5,206,023 A | * | 4/1993 | Hunziker | 424/423 |
| 5,209,776 A | * | 5/1993 | Bass | 106/124 |
| 5,290,552 A | * | 3/1994 | Sierra | 424/94.64 |
| 5,631,011 A | * | 5/1997 | Wadstrom | 424/400 |

FOREIGN PATENT DOCUMENTS

WO    WO-9202238    10/1997

OTHER PUBLICATIONS

Derwent Abstract 89–256457, 1989.
Derwent Abstract 92–079795, 1992.

* cited by examiner

Primary Examiner—Gollamudi S. Kishore
(74) Attorney, Agent, or Firm—Fish & Richardson P.C.

(57) ABSTRACT

A tissue treatment composition, especially an adhesive composition comprises (i) fibrin or fibrinogen and (ii) a biodegradable and biocompatible polymer capable of forming a viscous aqueous solution. In addition to glueing, the tissue adhesive composition may be used for slow-release of a drug incorporated into it or for anti-adherence purposes, for wound healing, etc.

22 Claims, 1 Drawing Sheet

Figure 1:
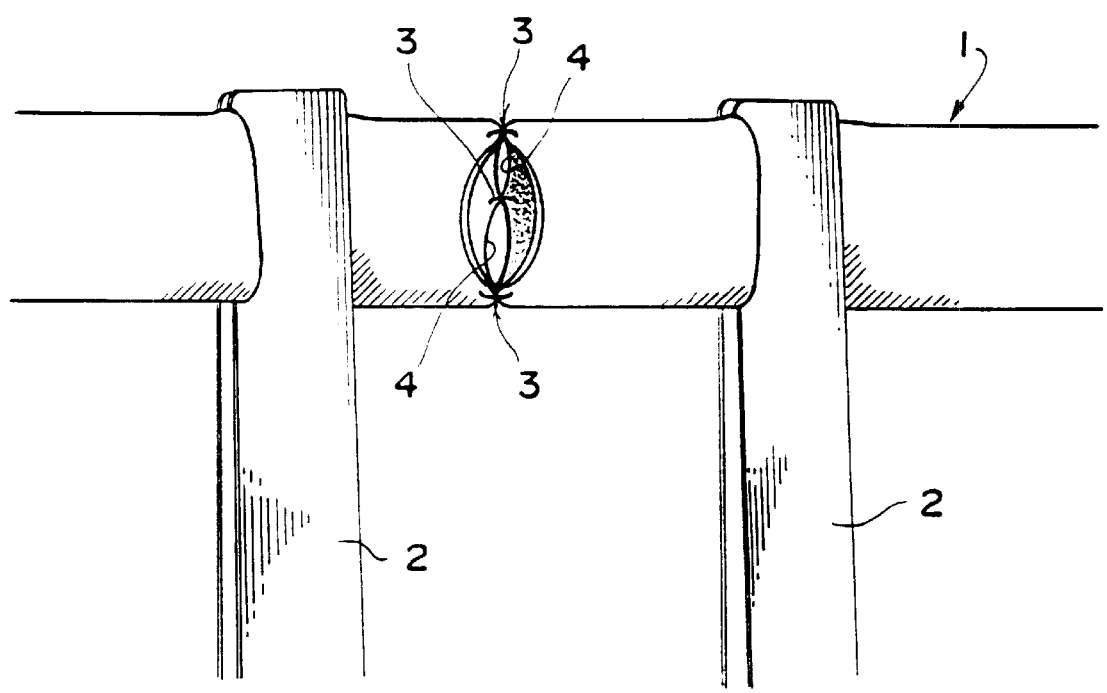

TISSUE TREATMENT COMPOSITION COMPRISING FIBRIN OR FIBRINOGEN AND BIODEGRADABLE AND BIOCOMPATIBLE POLYMER

This is a continuation of application Ser. No. 08/780,442, filed on Jan. 8, 1997, now abandoned, which is a continuation of application Ser. No. 08/162,078, filed on Feb. 7, 1994, now U.S. Pat. No. 5,631,011, which is a National Stage Proceeding under 35 U.S.C. §371 of International Application No. PCT/SE92/00441, filed on Jun. 17, 1992.

The present invention relates to a tissue treatment composition, especially a tissue adhesive having improved properties and to the use of such compositions as anti-adherence or would healing compositions, as slow-release drug formulations, for coating tissues or prosthetic materials, and as carriers for cell transplants.

The use of blood coagulating substances for stopping bleedings and for sealing wounds has been known for a long time. Thus, the hemostatic effect of fibrin powder was reported about 80 years ago, and attempts were made to employ fibrin or fibrin patches to stop bleeding in brain and general surgery.

Today such use of fibrin as a biologic adhesive has been widely accepted and found application in many fields of surgery. Generally fibrin sealants are based upon the two components fibrinogen and thrombin. As these components mix a fibrin coagulum is formed in that the fibrinogen molecule is cleaved through the action of thrombin to form fibrin monomers which spontaneously will polymerize to form a three-dimensional network of fibrin, largely kept together by hydrogen bonding. This corresponds to the last phase of the natural blood clotting cascade, the coagulation rate being dependent on the concentration of thrombin used.

In order to improve the tensile strength, covalent crosslinking between the fibrin chains is provided for by including Factor XIII in the sealant composition. The strength of the fibrin clot is further improved by the addition of fibronectin to the composition, the fibronectin being crosslinked and bound to the fibrin network formed.

To prevent a too early degradation of the fibrin clot by fibrinolys, the fibrin sealant composition may comprise a plasminogen activator inhibitor or a plasmin inhibitor, such as aprotinin. Such an inhibitor will also reduce the fibrinolytic activity resulting from any residual plasminogen in the fibrinogen composition.

Similarly, compositions according to the invention which include hyaluronic acid (or other polysaccharides), may also comprise a hyaluronidase inhibitor such as one or more flavonoids (or corresponding inhibitors for other polysaccharides) in order to prevent premature degradation (i.e. to prolong the duration) of the hyaluronic acid component by hyaluronidase which is always present in the surrounding tissues. The hyaluronic acid may, as mentioned above, be crosslinked, a commercially available example being Hylan® (trademark, available from Biomatrix, Ritchfield, N.Y., USA). The hyaluronic acid compositions may e.g. have the form of gels, solutions, etc.

The results obtainable by fibrin sealants are basically:
(i) Hemostasis. The fibrin clot acts as a hemostatic barrier and reduces the risk of serum, lymph and liquor leakage. The hemostatic effect may be enhanced if the fibrin sealant is combined with a biocompatible solid flat material such as collagen.
(ii) Glueing. Due to its adhesive properties the fibrin sealant atraumatically connects tissues by forming a strong joint between them and adapts uneven wound surfaces. This glueing effect is increased by fibronectin being bound to exposed collagen.
(iii) Wound healing. The fibrin sealant promotes the ingrowth of fibroblasts which in combination with efficient hemostasis and adhesion between the wound surfaces provides for an improved healing process. Wound healing promoted by fibrin sealants results in strong scar formation and does not prevent the formation of adhesions. The use of the compositions according to the invention as an anti-adherence/wound healing composition does, however, result in a normal (regenerative) tissue rather than scar tissue, i.e. optimal wound heaing. Furthermore, such compositions also reduce the inflammatory response as appears from the test results reported in Table 4 below.

Fields of application include among others: ear, nose and throat surgery, general surgery, dentistry, neurosurgery, plastic surgery, thorax and vascular surgery, abdominal surgery, orthopaedics, accident surgery, gynaecology, urology, and opthalmology. Fibrin sealants have also been used for local application of drugs, such as antibiotics, growth factors and cytostatics.

Commercial fibrin glues (prepared from human plasma) are available under the trade names Tissucol, Tisseel and Fibrin-Kleber Humano Immuno (Immuno AG, Vienna, Austria) as well as Beriplast (Behringwerke AG, Marburg, Germany) (these trade names being registered trademarks in several countries). Tisseel™ is a two-component kit containing a fluid thrombin component including calcium chloride and a somewhat more viscous fibrinogen component including factor XIII, fibronectin, aprotinin and plasminogen. The two components are delivered deep frozen in two separate syringes, or as two lyphilized powders with corresponding aprotinin and calcium solutions as solvents. As explained above the fibrin sealant consolidates when the two components are combined due to fibrin monomer aggregation. The setting rate is dependent on the thrombin concentration and varies from a few seconds (high thrombin concentration) to a couple of minutes (low thrombin concentration).

However, an important and well known disadvantage of the known preparations resides in the water-like fluidity of the components when applied, which leads to considerable handling difficulties of the glue. Efforts have been made to overcome this problem and facilitate the mixing of the components by the development of particular application modes such as a double-syringe applicator (e.g. that supplied under the trade name Duploject®, Immuno AG, Vienna, Austria, and which is disclosed in e.g. U.S. Pat. No. 4,359, 049, or a special spray system as disclosed in e.g. EP-A-156 098). The basic problem with a low viscosity glue still remains, however. Firstly, a non-viscous or low viscosity glue is unsuitable for use on non-horizontal surfaces since it will run off before setting. Secondly, there is a definite risk of a non-viscous or low vicosity glue running off to sites where it is unwanted and where it might cause complications. This is particularly the case in vascular surgery since the fluid glue may reach inside the vessels before it sets and thereby cause thromboembolic complications. An instantaneously setting fibrin glue (containing a high concentration of thrombin), on the other hand, cannot be used where the parts to be sealed require subsequent adaptation.

A different approach has been disclosed by i.a. Bass et al in J. Vasc. Surg. May 11, 1990 (5):718–25, which is incorporated herein by reference. This paper discloses a technique called laser tissue soldering (or welding), wherein a laser energy absorbing dye (chromophore) and fibrinogen are soldered by means of a laser to produce a strong anastomosis which is said to be i.a. faster healing than a conventional sutured anastomosis. Similar coagulation and/or bonding effects can be achieved with other proteins and energy sources.

It is an object of the present invention to provide an improved fibrin glue which is devoid of the above low viscosity problem, and which promotes wound healing without scar formation or development of adhesions. This object is achieved by including in a fibrin glue composition of the above mentioned type a viscosity increasing amount of a biodegradable and biocompatible polymer capable of forming a viscsous aqueous solution. In accordance with the present invention it has thus been found that by the addition of such a viscosity enhancing polymer, the glue composition will obtain a viscosity adequat to facilitate and improve the handling and application thereof, while not negatively affecting the favourable properties of the fibrin glue. For wound healing and anti-adherence purposes the adhesive properties may, however, be less pronounced, or even missing.

Accordingly, the present invention relates to a tissue treatment composition comprising (i) fibrin or fibrinogen and (ii) a biodegradable and biocompatible polymer capable of forming a viscous aqueous solution, optionally also other proteins.

One use form of the present tissue adhesive composition is thus an improved fibrin sealant or glue which upon use exhibits viscosity characteristics permitting easy and safe application thereof at a desired location or site.

In another use form the present tissue treatment composition comprises a therapeutical substance and constitutes a pharmaceutical composition for local administration of the therapeutical substance. In a particular embodiment the therapeutical substance is the viscous polymer itself or a species coupled thereto as will be described in more detail below.

Still another use form of the present tissue treatment composition is a wound healing and an anti-adherence composition, the high molecular composition conferring such adherence-preventing properties to the composition that it may be used for preventing the adherence of adjacent tissues in surgical procedures. Related to such anti-adherence use is the use of the present tissue treatment composition for wound healing. By, for example, glueing wound edges with the tissue treatment, neat scars will be obtained. Further, cellular translplants, in particular dermal transplants, will heal faster. This would, of course, be of particular interest in plastic surgery.

The above mentioned biodegradable and biocompatible polymer capable of forming an aqueous solution may be selected from a wide variety of substances (including substances which will be available in the future) and the selection thereof can readily be made by the person skilled in the art.

A preferred group of said biodegradable and biocompatible polymers, hereinafter frequently referred to as viscosity enhancing polymers, consists of high molecular polyglycans or polysaccharides. Exemplary of such polysaccharides for the purposes of the invention are xanthan, dextran, cellulose and proteoglycans, especially hyaluronic acid, and salts and derivatives thereof. As examples of cellulose derivatives may be mentioned methyl cellulose, carboxymethyl cellulose (CMC) and hydroxy-propylmethyl cellulose (HPMC), just to mention a few thereof. Examples of viscosity enhancing polymers other than high molecular polysaccharides are gelatin and polyvinylpyrrolidone.

A preferred polysaccharide/polyglycan is hyaluronic acid and salts and derivatives thereof. Sodium hyaluronate is a high molecular weight linear polysaccharide built up of repeating disaccharide units. It exists in the extracellular space of all tissues and has the same simple chemical structure n all species. Hence, the application of a purified preparation of hyaluronate results in but a temporary increase of the local concentration of endogenous material and its utilization in the composition will therefore not have any detrimental physiological effects. In solution the hyaluronate adopts a conformation of very extended random coils, that already at low concentrations entangle into a flexible molecular network that gives hualuronate solutions interesting rheological properties that are useful for the present purposes.

The visco-elastic properties of sodium hyaluronate has lead to its clinical use as spacer and to facilitate operative procedures in the field of eye surgery. It has also been demonstrated to be biologically active in enhancing epithelial regeneration of the ear tympanic membrane and to inhibit the ingrowth of vascular endothelial cells. Further, it plays a role in wound healing, influencing the migration of granulation tissue cells and reduces the amount of adhesions formed after surgery. The bioavailability of sodium hyaluronate per se is, however, limited due to its rapid turnover and short half-life.

When the tissue treatment composition is used as an improved tissue adhesive, the proportion of the viscosity enhancing polymer in the fluid fibrin glue as applied should be selected to provide an appropriate viscosity for the intended application while not adversely interfering with the fibrin clotting, and will depend on the polymer and the particular tissue adhesive composition to be produced. Suitable initial viscosities of the final solution mixture of the total composition for each particular application may readily be established by the skilled person, but will generally be in the range of about 500 to about 1,000,000 centipoises (cP), preferably about 1,000 to about 500,000 centipoises. The term "final solution mixture" as used herein does not necessary mean a homogeneous state. On the contrary, depending on the mixing procedure, the mixture will in many cases not reach a homogeneous or uniform state before clotting. As is well known to the person skilled in the art, the viscosity is correlated to concentration and limiting viscosity number, $\eta_0 = (Conc. \times [\eta])^{3.6}/10$. Modified after Morris et al, Carbohydrate polymers, Vol. 1, 1981, p. 5–21. From $[\eta]$ we get the molecular weight using Cleland's formula for $[\eta] = k \times$ average molecular weight$^{k1}$, Cleland et al, Biopolymers, Vol. 9, 1970, p. 799–80.

Like the prior art fibrin sealants the tissue adhesive composition of the present invention may comprise additional constituents. Thus, in addition to sealer protein and viscosity enhancing polymer, such as e.g. high molecular polysaccharide, the Composition will preferably comprise Factor XIII and/or fibronectin and/or plasminogen. Advantageously, the composition will also include clotting enzyme, i.e. thrombin, especially in combination with bivalent calcium, such as calcium chloride. The concentration of calcium chloride will then vary) e.g. between 40 mM to 0.2 M depending on the specific purpose of the tissue adhesive composition, high concentrations of calcium chloride inhibiting fibroblast growth and therefore being preferred for anti-adherence applications (along with absence of fibronectin which stimulates the ingrowth of fibroblasts). It may further be valuable to include a fibrinolysis inhibitor, such as a plasmin inhibitor, e.g. aprotinin, aprilotinin, alpha-2-antiplasmin, alpha-2-macroglobulin, alpha-1-antitrypsin, epsilon-aminocaproic acid or tranexamic acid, or a plasmin activator inhibitor, e.g. PAI-1 or PAI-2.

While the proportions of the previously known ingredients in the tissue adhesive compositions of the invention may be selected with guidance of prior art compositions, the necessary amount of the viscosity enhancing polymer can readily be determined by a person skilled in the art depending on the particular polymer and the intended use form. Thus, if the concentration and/or molecular weight of the viscosity enhancing polymer is too low, the viscosity increase will be insufficient, and a too high concentration and/or molecular weight will inhibit the fibrin polymerization and the adhesion to the tissue.

By increasing the thrombin concentration, the polymerization of fibrinogen may be speeded up with a consequential influence on the time until the glue sets. At low thrombin concentrations the fibrin glue composition will remain more or less fluid for several minutes after application. A further beneficial effect of increasing the viscosity with a viscosity enhancing polymer in accordance with the invention is therefore the possibility to use lower concentrations of thrombin, which is required in situations where the parts to be sealed require subsequent adaptation even on non-horizontal surfaces.

The tissue treatment composition of the present invention may be presented in the same type of preparations as the prior art fibrin sealants. In an advantageous embodiment the tissue adhesive is therefore a two-component preparation, one component comprising the blood clot protein(s) and the other comprising thrombin and bivalent calcium as well as possible additives including fibrinolysis inhibitors. The viscosity enhancing polymer may be contained in one or both of the two components depending on the intended use of the tissue adhesive. While in the case of a fibrin glue the viscosity enhancing polymer may be contained in either or both of the two components, it is for other applications preferably associated with the fibrin or fibrinogen component. It is, of course, at least theoretically, also possible to provide the viscosity enhancing polymer as a separate component. The components may be provided in deep frozen solution form or as lyophilized powders, to be diluted prior to use with appropriate aqueous solutions, e.g. containing aprotinin and calcium ions, respectively.

The tissue treatment composition of the invention may also be used in various combinations as is per se known in the art. For example, with reference to the above mentioned two-component embodiment, one component may be provided in a biocompatible solid matrix material as a prefabricated unit and the other (activating) component may be added at the time of use. The viscosity enhancing polymer may then be provided together with any one or both of said components.

In such an embodiment the tissue adhesive of the invention may include a tissue-compatible flat matrix material, such as a non-woven fabric, into which the blood coagulation substance, the viscosity enhancing polymer, e.g. high molecular polysaccharide, and optional additional constituents are impregnated. In a variation the viscosity enhancing polymer is added together with the thrombin. In another variation the matrix material is impregnated with the thrombin, and the blood coagulation substance is added together with the viscosity enhancing polymer at the time of use. Such a non-woven fabric may, for example, be a glycoprotein, such as collagen (preferably porous), globulin, myoglobulin, casein or albumin; gelatin; silk fibroin or a polysaccharide, such as cellulose; or mixtures thereof. Such an embodiment will, for instance, be particularly useful for stopping bleedings and covering wounds. It is to be noted, however, that, as will be readily understood, for anti-adherence purposes a material like collagen having adhesion enhancing properties would not be appropriate; cellulose e.g. being a more suitable material in this respect. Such an impregnated flat material is advantageously provided in lyophilized form.

In another embodiment the tissue treatment composition is provided as a film or sheet for surgical use comprising a non-crosslinked combination of fibrin and viscosity enhancing polymer.

The tissue treatment composition of the present invention may, of course, be used in all other preparations in which the prior art fibrin glues have been presented, e.g. as an implantation material for joint cartilage and bone defect repair material in combination with embryonic chondrocytes or mesenchymal cells, such as described for a conventional fibrin glue in e.g. U.S. Pat. No. 4,642,120.

As already mentioned above the present tissue treatment composition, e.g. in any one of the above described embodiments, may be used for the application of a pharmaceutically active substance. By incorporating a drug, such as an antibiotic, a growth factor, etc. into the tissue adhesive it will be enclosed in the fibrin network formed upon application of the tissue adhesive. It will thereby be ensured that the drug is kept at the site of application while being controllably released from the composition, e.g. when used as ocular drops, a wound healing preparation, etc.

As also mentioned above the pharmaceutically active substance to be released from the present tissue adhesive composition may be the viscosity enhancing polymer in itself or a substance coupled thereto.

A specific example of such a viscosity enhancing polymer fulfilling the viscosity enhancing requirement as well as having therapeutical and pharmaceutical utility, and for which it may be desired to sustain the bioavailability, is hyaluronic acid and salts and derivatives thereof which are easily soluble in water and, as mentioned previously, have an extremely short biological half-life. The tissue treatment composition of this invention thus constitutes an advantageous slow-release preparation for proteoglycans such as hyaluronic acid and its salts and derivatives, and considerably increases the bioavailability thereof.

The tissue treatment composition of the present invention may, for example, be prepared and provided in administration forms in analogous manner as the prior art tissue adhesives.

It should be emphasized that the compositions are not restricted to the adhesive properties, but non-adhesive compositions are also included, especially when the compositions primarily are intended for wound healing. The latter compositions may in particular include non-adhesive proteins such as albumin and/or growth factors. Substantially non-adhesive compositions may also be obtained when the polymer part of the composition inhibits the adhesive properties of the protein part. It should in this context be emphasized that the invention comprises both adhesive and substantially non-adhesive compositions, although it has for simplicity reasons often has been referred to as an "adhesive" in this specification, including the Examples.

In the following the invention will be described in more detail by way of non-limiting examples. In one example the gluing properties of an embodiment of the tissue adhesive composition are tested in animal experiments, reference being made to the accompanying drawing in which the only figure is a schematic side view of a clamped vessel with three sutures. A second example describes the preparation of another embodiment of tissue adhesive composition. A third example illustrates the use of the tissue treatment composition as a controlled release preparation, and a fourth example shows the properties of the tissue treatment composition as an anti-adhesion and wound healing promoting agent.

A BRIEF DESCRIPTION OF THE DRAWINGS

FIG. 1 is schematic illustration of a gap of 0.2–0.4 mm between each suture caused by the tension of the vessel.

EXAMPLE 1

Animals

Twentyone male Sprague-Dawley rats with a body weight of 230–345 g were used. They were housed under standardized environmental conditions, with free access to water and food, for one week prior to the experiments.

Operative Procedure

The animals were anaesthetized with fluanisone; 0.75 mg/100 g b.w. and fenatyl; 0.024 mg/100 g b.w., (Hypnorm®, Janssen, Belgium), in combination with midazolan; 0.38 mg/100 g b.w., (Dormicum®, Roche AG, Switzerland) given subcutaneously. An additional dose was given after 30-45 minutes.

The animals were placed on a warming water blanket (Aquamatic K-20-D, Hamilton, Cinn., USA) which was set at 37° C.

The femoral vessels were exposed through an L-shaped groin incision and the artery was mobilized from the inquinal ligament to the epigastric vessels. The profunda artery was cauterized with bipolar diathermia. A few $\mu l$ of papaverine, 40 mg/ml, (ACO), Sweden), were administered topically to resolve vasospasm induced by the operative trauma. Two to three minutes later two separate microvascular clamps were applied and the artery divided with a pair of scissors. The cut ends of the vessel were gently dilated with a microdilator and the lumina washed out with a few milliliters of saline. The artery was then sutured with three 10.0 nylon sutures (STT) placed at 120° from each other. The tension of the vessel caused a gap of 0.2–0.4 mm between each suture as is schematically illustrated in FIG. 1, wherein reference numeral 1 designates the vessel, 2 represents clamps, 3 designates sutures, and 4 indicates said gaps.

Instead of completing the anastomosis, which generally requires a total of 8–12 sutures, the gap between the stitches were sealed with 0.2 ml of fibrin glue applied with a Duploject® double-syringe system (Immuno AG, Austria). The glueing procedure of the anastomosis was randomized to one of the three following glue preparations:

I. Original Tisseel® (Immuno AG, Austria) in which one syringe ("Fibrinogen gen component") contained 75–115 mg(ml of fibrinogen, 2–9 mg/ml of plasma fibronectin, 10–50 U of Factor XIII, 40–120 $\mu l$ of plasminogen and 3000 KIU/ml of aprotinin, and had a viscosity of about 100 cP. The other syringe ("Thrombin component") contained 500 IU/ml of thrombin and 40 mM $CaCl_2$ and had a viscosity of 1.2 cP. The initial viscosity of the mixed contents (1+1) of the two syringes was well below 100 cP.

II. The Tisseel® Fibrinogen component was mixed 1+1 with sodium hyaluronate solution, 10 mg/ml, with an average molecular weight of 4,000,000, zero shear viscosity 300,000 cP, dissolved in 0.002 M Na-phosphate, 0.145 M NaCl, pH 7.3 (Healon®, Kabi Pharmacia AB, Sweden); the addition of hyaluronate thus reducing the final concentrations of aprotinin and fibrinogen by one half and providing a viscosity of about 24,000 cP. The initial viscosity of the solution obtained upon mixture (1+1) of the hyaluronate-supplemented Fibrinogen component with the Thrombin component was about 2,000 cP.

III. The Fibrinogen component was diluted 1+1 with 0.145 M NaCl, leading to the same final concentrations of aprotinin and fibrinogen as in preparation II.

Five minutes after glue application the vascular clamps were removed, beginning with the distal one. Occasional bleeding was controlled by gentle manual compression.

Test Procedure and Results

The patency was tested 20 minutes after completion of the anastomosis with Aucland's patent test (Aucland R. D., Microsurgery Practice Manual, 2nd Ed. 1980, Mosby, St. Louis). The skin was then closed with interrupted sutures and the animals were allowed to awaken from the anaesthesia.

The animals were re-evaluated 24 hours later in a blind fashion. The animals were anaestetized and the patency of the anastomosis was tested as described above. The rats were then killed with an overdose of barbiturate and the patent arteries were excised. Excessive fibrin glue was removed, and the vessel and the anastomosis were then incised longitudinally and inspected from inside. Intravascular thrombus material was gently removed by flushing with saline and remaining wall adherent fibrin glue deposits were semi-quantitatively assessed in percent of the internal vessel diameter.

The effects of the three types of glue preparations on the patency of the anastomosis and fibrin glue deposits were evaluated by comparing groups I, II and III with the use of a one-way ANOVA with multiple range testing according to the method of least significant differences, 20 minutes and 24 hours, respectively, after completion of the anastomosis. All data were given as mean+SEM. A difference at the 5% level was regarded as significant. The results are summarized in Table 1 below.

TABLE 1

| | Experimental groups | | |
|---|---|---|---|
| | I<br>Original<br>Tisseel[R] | II<br>Diluted with<br>hyaluronate | III<br>Diluted with<br>saline |
| Patency rates (%) | | | |
| 20 min postop.<br>Fibrin mass inside<br>the patent vessels<br>in % of vessel<br>diameter | 35.7 ± 13.3 | 85.7 ± 9.7 | 35.7 ± 13.3 |
| 24 h postop. | 37.5 ± 11.9 | 8.0 ± 4.2 | 47.9 ± 11.1 |

As appears form the table the patency 20 minutes after completion of the anastomosis was significantly higher ($p<0.01$) in group II than in groups I and III. The semi-quantitative determination of the amount of fibrin mass which reached inside the patent vessels was significantly lower in sodium hyaluronate treated fibrin preparations than in groups I and III.

The patency rates achieved in the present study are comparable to those previously reported on microvascular anastomosis performed with a minimal number of sutures combined with additional fibrin glue (50–75%), (see e.g. Aucland R. D., supra).

The patency rate 20 minutes after completion of the anastomosis was thus significantly higher in the group where Tisseel® was combined with sodium hyaluronate. This improvement is due to an increased viscosity of the preparation and not a dilution of fibrin, which is demonstrated by the fact that dilution with saline did not influence the patency rates. This mechanism is further demonstrated by the fact that less fibrin reached inside the vessel in the sodium hyaluronate treated group.

EXAMPLE 2

A fibrin glue composition corresponding to composition II in Example 1, but wherein xanthan was substituted for hyaluronic acid, was prepared by mixing 1 part (volume) of the Fibrinogen component of original Tisseel® (Immuno AG, Austria), which had the same composition as given in Example 1, with 1 part (volume) of a 10 mg/ml aqueous xanthan solution having a zero shear viscosity of 1,000,000 cP. The resulting solution containing Tisseel® and xanthan, and having a viscosity of 80,000 cP, was then mixed (1+1) with the Tisseel® Thrombin component (500 IU/ml; viscosity 1.2 cP). The subsequent clotting of fibrin in the resulting mixture, which had an initial viscosity of about 6,400 cP, was followed with a rheometer at 37° C. After 30 minutes the phase angle was about 4° C. and the elastic (storage) modulus was 1,300 Pa.

For comparison, 1 part (volume) of the Fibrinogen component of original Tisseel® was mixed with 1 part (volume) of saline (0.15 M NaCl). The resulting fibrinogen containing solution was mixed with the Thrombin component (500 IU/ml) and the fibrin clotting was followed as above at 37° C. After 30 minutes the phase angle was about 2° and the elastic (storage) modulus was 1,800 Pa.

Thus, in both cases very elastic gels (phase angle close to 0°) of approximately the same stiffness (elastic modulus) were formed at 37° C.

EXAMPLE 3

Test Procedure

1% (10 mg/ml) sodium hyaluronate (NaHA) (Healon®, Kabi Pharmacia, Uppsala, Sweden) was mixed 1+1 with the aprotinin and fibrinogen containing syringe of Tisseel® fibrin glue (Immuno AG, Vienna, Austria) as described for glue preparation II in Example 1. The second, thrombin containing component of the fibrin glue was added with the Duploject® applicator (Immuno AG, Vienna, Austria) leading to a final concentration of 0.25% NaHA. 100 mg of the final composition were placed at the bottom of a petri dish. After a setting time of one minute (group A) and 10 minutes (group B) later, 10 ml of 0.145 M NaCl were added. The petri dishes were either put in a shaking bath with a frequency of 1 Hz at 37° C., or at rest in a humidified tissue culture chamber set at 37° C. (groups C and D, respectively).

The corresponding controls were 1% NaHA (Healon®) diluted 1+3 with 0.145 M NaCl, leading to the same final concentrations of NaHA as in the experimental groups (0.25%). The controls were treated in the same manner as the experimental groups with shaking (groups AC and BC) and without shaking (groups CC and DC). Samples of the added NaCl solution were taken after 30 min, 60 min, 4 h, 8 h and 24 h for analysis of NaHA. The NaHA concentrations of the NaCl solution were determined with the HA Test 50 (Kabi Pharmacia AB, Uppsala, Sweden).

Results

In the control groups the NaCl solutions were almost immediately saturated and there was practically no further increase in NaHA concentration up to 24 h, irrespectively of whether the samples were put at rest or shaken. In the experimental groups, on the other hand, the concentration of NaHA in the NaCl solution increased steadily. The dissolution rates were depending on whether the fibrin clots were allowed to set for 10 min before adding the NaCl solution, and whether they were put at rest or shaken. The results are summarized in the following Table 2.

TABLE 2

| | NaHA conc. in added NaCl-solution (µg/ml) | | | | | | | |
|---|---|---|---|---|---|---|---|---|
| | Experimental groups | | | | Control groups | | | |
| | Shake | | Rest | | Shake | | Rest | |
| Time | A | B | C | D | AC | BC | CC | DC |
| 30 min | 2.4 | 0.7 | 1.3 | 0.5 | 23 | 27 | 26 | 27 |
| 24 h | 21 | 25 | 23 | 15 | 33 | 29 | 28 | 36 |

To express how fast NaHA was dissolved. the time until 30% of the final amount of A was found in the NaCl solution was calculated. The results are summarized in Table 3 below.

TABLE 3

| Dissolution time until 30% of NaHA in solution (min.) | | | | | | | |
|---|---|---|---|---|---|---|---|
| Experimental groups | | | | Control groups | | | |
| Shake | | Rest | | Shake | | Rest | |
| A | B | C | D | AC | BC | CC | DC |
| 15 | 36 | 336 | 462 | 3 | 3 | 3 | 3 |

The above results clearly show that sodium hyaluronate dissolves up to 150 times slower in a saline solution when it is incorporated in a fibrin clot. The dissolving rate is very much dependent upon how long the fibrin glue is allowed to set before the solvent is added. It can be expected that the dissolution rate will decrease further if the clot is allowed to set for still longer periods of time since it will take several hours to complete the crosslinkage of the fibrin bundles. It is further demonstrated that the mixture of NaHA and fibrin should not be under motion if a prolongation of the dissolution rate is desired.

EXAMPLE 4

Animals and Test Procedure

Ten male Sprague Dawley rats with a body weight of 440–480 g were used. The environmental conditioning and the anaesthesia were the same described in Example 1 above. A laparotomy was performed through a midline incision. A titanium disc having a 11 mm diameter circular hole in the middle was placed on the surface of the right anterior liver lobe. The serosal surface of the liver exposed in the hole of the disc was gently brushed with a nylon interdental tooth brush until petechial bleeding was achieved. A somewhat larger area of the parietal peritoneum was traumatized in the same manner. The location of the traumatized parietal surface was chosen so that the two brusched surfaces should be in direct contact with each other. Previous studies have shown that solid adhesions develop only at the location where both serosal surfaces are in direct contact. Five animals were each allocated to either no treatment or to treatment with a mixture of hyaluronate and fibrin glue as described for glue preparation II in Example 1. In the second case the circumscribed lesion he liver surface was covered with 0.4 ml of the hyaluronate and fibrin glue mixture. Hyaluronate was added and mixed 1+1 with the contents of the fibrinogen containing syringe of Tisseel® (glue preparation II in Example 1 above).

The rats were kept on their backs for 20 minutes after application of the mixture to assure that parietal and visceral surfaces were not in contact during the setting of the glue. The abdomen and skin were then closed in layers with a running 4.0 Dexon suture. The animals were sacrificed after 48 days. The abdomen was re-exposed through a midline incision and the adhesions were evaluated. The occurrence and the area of adhesions developed were expressed in percent of the initial serosal damage.

The effect of the hyaluronate-fibrin glue on the development of adhesions was evaluated by means of an unpaired tow-tailed t test. Data are given as mean+SEM. A difference at the 5% level was regarded as significant.

Results

All adhesions found were located between the liver and the inner surface of the abdominal wall, localized to the area where the liver surface had been traumatized with the brush. All but one of the animals in the control group developed adhesions whereas none of the animals of the treatment group developed any adhesions. The results are presented in Table 4 below.

TABLE 4

|  | Control group | Treatment group |
|---|---|---|
| Occurrence of adhesions (number of animals, %) | 80 ± 20* | 0 ± 0 |
| Inflammatory reactions (0–3) | 1.2 ± 0.4 | 0.8 ± 0.2 |
| Adherence area (%) | 65 ± 23.8* | 0 ± 0 |

*significant at 5% level

The combined treatment with hyaluronate and fibrin glue thus completely abolished the development of adhesions, something that has so far not been achieved with either treatment alone (Lindenberg S., et al., Acta Chir, Scand. 151:525–527, 1985; and Amiel D., et al., J. Hand. Surg. (Am) 14:837–843, 1989). The mechanisms behind this finding are unclear. The fact that hyaluronate is kept at the location of trauma for a longer period of time as well as the changed composition of the fibrin clot seems to optimize the conditions for wound healing and prevent the formation of excessive scar tissue.

Furthermore, the composition also markedly reduced the inflammatory reaction, which indicates that the wound healing is induced by regeneration rather than formation of scar tissue and shrinkage.

It is to be understood that when reference is made herein to e.g. "polymers", "proteins", "polysaccharides", "polyglucans", and the like, then the invention also includes salts, derivatives and other modifications thereof which are functionally equivalent as regards the herein disclosed properties.

What is claimed is:

1. A tissue treatment composition consisting essentially of the following components:
   (i) factor XIII;
   (ii) fibrinogen;
   (iii) thrombin and optionally bivalent calcium;
   (iv) at least one component selected from the group consisting of a viscosity enhancing polysaccharide and a viscosity enhancing proteoglycan which is capable of forming a viscous aqueous solution; and
   (v) optionally at least one member selected from the group consisting of fibronectin, a plasmin inhibitor, a plasminogen activator inhibitor, and plasminogen;
   with the proviso that said fibrinogen containing component is separate from said thrombin containing component until said components are mixed together at the time of treatment; and with the proviso that said composition, upon said mixing of the components, has an initial viscosity in the range of about 500 to 1,000,000 cP.

2. A tissue treatment composition in the form of a film or sheet which may be pre-formed, said composition consisting essentially of the following components:
   (i) factor XIII;
   (ii) fibrinogen;
   (iii) thrombin and optionally bivalent calcium;
   (iv) at least one component selected from the group consisting of a viscosity enhancing polysaccharide and a viscosity enhancing proteoglycan which is capable of forming a viscous aqueous solution; and
   (v) optionally at least one member selected from the group consisting of fibronectin, a plasmin inhibitor, a plasminogen activator inhibitor, and plasminogen.

3. A slow-release drug formulation which consists essentially of the following components:
   (i) factor XIII;
   (ii) fibrinogen;
   (iii) thrombin and optionally bivalent calcium;
   (iv) at least one wound healing promoting protein;
   (v) at least one component selected from the group consisting of a viscosity enhancing polysaccharide and a viscosity enhancing proteoglycan which is capable of forming a viscous aqueous solution; and
   (vi) optionally at least one member selected from the group consisting of fibronectin, a plasmin inhibitor, a plasminogen activator inhibitor, and plasminogen;
   with the proviso that said fibrinogen containing component is separate from said thrombin containing component until said components are mixed together at the time of treatment; and with the proviso that said composition, upon said mixing of the components, has an initial viscosity in the range of about 500 to 1,000,000 cP.

4. A tissue treatment composition according to claim 1, wherein said composition contains at least one member selected from the group consisting of fibronectin, a plasmin inhibitor, a plasminogen activator inhibitor, and plasminogen.

5. A tissue treatment composition according to claim 1, wherein said thrombin containing component contains bivalent calcium.

6. A tissue treatment composition according to claim 1, wherein said viscosity enhancing polysaccharide is selected from the group consisting of xanthan, dextran, cellulose and glycosaminoglycans, and salts and derivatives thereof.

7. A tissue treatment composition according to claim 6, wherein said viscosity enhancing glycosaminoglycan is hyaluronic acid, crosslinked hyaluronic acid or a salt or derivative thereof.

8. A tissue treatment composition according to claim 1, wherein said initial viscosity is in the range of about 1,000 to 500,000 cP.

9. A tissue treatment composition according to claim 5, wherein one of said thrombin containing component and said fibrinogen containing component is supported on a solid matrix or carrier material.

10. A tissue treatment composition according to claim 7, for the administration of hyaluronic acid, crosslinked hyaluronic or a salt thereof.

11. A tissue treatment composition according to claim 1, wherein the composition is in deep-frozen or lyophilized form.

12. A tissue treatment composition according to claim 1, wherein the composition is a tissue adhesion composition.

13. A slow-release drug formulation which comprises a tissue treatment composition according to claim 1.

14. The slow-release drug formulation according to claim 3, wherein said at least one wound healing promoting protein is selected from the group consisting of serum proteins, tissue growth factors, hormones, and chemotactic proteins.

15. A tissue treatment composition as claimed in claim 1, which is a wound healing promoting composition.

16. A tissue treatment composition as claimed in claim 1, which is a scar formation reducing composition.

17. A method for producing a viscous tissue treatment composition comprising mixing in arbitrary order
 (i) factor XIII;
 (ii) fibrinogen;
 (iii) thrombin, and
 (iv) a viscosity enhancing polysaccharide or proteoglycan which is capable of forming a viscous aqueous solution.

18. The slow-release drug formulation according to claim 13, wherein a pharmaceutically active substance is coupled to said viscosity enhancing polymer.

19. The composition of claim 1 wherein component (iv) is a viscosity enhancing proteoglycan.

20. The method of claim 17 wherein component (iv) is a viscosity enhancing proteoglycan.

21. The tissue treatment composition of claim 2 wherein component (iv) is a viscosity enhancing proteoglycan.

22. The drug formulation of claim 3 wherein component (v) is a viscosity enhancing proteoglycan.

* * * * *